United States Patent
Keith, Jr. et al.

(10) Patent No.: US 6,723,314 B2
(45) Date of Patent: Apr. 20, 2004

(54) USE OF INTERLEUKIN-11 TO TREAT GASTROINTESTINAL DISORDERS

(75) Inventors: James C. Keith, Jr., Andover, MA (US); Theo L. Peeters, Linden (BE); Inge Depoortere, Bonheiden (BE); G. Van Asche, Leuven (BE)

(73) Assignees: Genetics Institute, LLC, Cambridge, MA (US); Catholic University, Leiden (BE)

(*) Notice: Subject to any disclaimer, the term of this patent is extended or adjusted under 35 U.S.C. 154(b) by 0 days.

(21) Appl. No.: 09/920,532

(22) Filed: Aug. 1, 2001

(65) Prior Publication Data

US 2001/0046482 A1 Nov. 29, 2001

Related U.S. Application Data

(63) Continuation of application No. 09/545,627, filed on Apr. 7, 2000.
(60) Provisional application No. 60/129,421, filed on Apr. 15, 1999.

(51) Int. Cl.$^7$ ............................................. A61K 38/19
(52) U.S. Cl. ...................................... 424/85.2; 530/351
(58) Field of Search .............................. 424/85.2; 514/2

(56) References Cited

U.S. PATENT DOCUMENTS

| | | | |
|---|---|---|---|
| 5,215,895 A | | 6/1993 | Bennet et al. |
| 5,270,181 A | | 12/1993 | McCoy et al. |
| 5,292,646 A | | 3/1994 | McCoy et al. |
| 5,679,339 A | | 10/1997 | Keith et al. |
| 5,700,664 A | | 12/1997 | Yang et al. |
| 5,958,401 A | | 9/1999 | Keith et al. |
| 6,126,933 A | * | 10/2000 | Warne et al. |

OTHER PUBLICATIONS

A. Pennathur et al., Erythromycin strengthens the defective lower esophageal sphincter in patients with gastroesophageal reflux disease. 1994. Am J Surg. 167(1): 169–73.*

T. Yokoyama et al. Recovery of gastrointestinal motility from post–operative ileus in dogs: effects of Leu13–motilin (KW–5139) and prostaglandin F2 alpha. 1985. Neurogastroenterol Motil. 7(4): 199–210.*

C.L. Berseth. Gastrointestinal motility in the neonate. 1996. Clin Perinatol, 23(2): 179–90.*

A.J. Smith et al. Prokinetic effect of erythromycin after colorectal surgery: randomized, placebo–controlled, double–blined study. 2000. Dis Colon Rectum, 43(3): 333–7.*

E. Ng et al. Erythromycin for feeding intolerance in preterm infants. 2000. Cochrane Database Syst Rev, 2000 (2): CD001815.*

B.Y. De Winter et al. Effect of different prokinetic agents and a novel enterokinetic agent on postoperative ileus in rats. 1999. Gut, 45(5): 713–8.*

N. Inatomi et al. An erythromycin derivative, EM–523, induces motilin–like gastrointestinal motility in dogs. 1989, J Pharmacol Exp Ther, 251(2): 707–12.*

I. Depoortere et al. Differential changes in ACh–, motilin–, substance P–, and K(+)–incuced contractility in rabbit colitis. 1999. Am J Physiol, 277 (1 Pt 1):G61–8.*

A. R. Zlatkina et al. The current pathogenic aspects of diarrhea in ulcerative colitis. 1994. Terapevticheskii Arkhiv, 66(12): 67–70.*

H.S. Besterman et al. Gut hormones in inflammatory bowel disearse. 1983, Scand J Gastroenterol, 18: 845–852.*

I. Depoortere et al. Dose–dependent effects of recombinant human interleukin–11 on contractile properties in rabbit 2,4,6–trinitrobenzene sulfonic acid colitis. 2000. J Pharmacol and Exp Ther, 294: 983–990.*

X.X. Du et al. A bone marrow stromal–derived grouwth factor, interleukin–11, stimulates recovery of small intestinal mucosal cells after cytoablative therapy. 1994. Blood, 83:33.*

Siadati and Sarr.(1998). Role of extrinsic innervation in release of motilin and patterns of upper gut canine motility. *J. Gastrointest. Sur.* 2(4): 363–72.

Luiking, et al.(1998). Motilin induces gall bladder emptying and antral contractions in the fasted state in humans. *Gut* 42(6): 830–5.

Depoortere, et al. (1997). Distribution and subcellular localization of motilin binding sites in the rabbit brain. *Brain Res.* 777(1–2):103–9.

Van Assche, et al. (1997). Concentration–dependent stimulation of cholinergic motor nerves or smooth muscle by [Nle13]motilin in the isolated rabbit gastric antrum. *Eur. J. Pharmacol.* 337(2–3): 267–74.

Tomita, et al. (1997). The role of motilin and cisapride in the enteric nervous system of the lower esophageal sphincter in humans. *Surg. Today.* 27(11): 985–92.

Boivin, et al. (1997). Neural mediation of the motilin motor effect on the human antrum. *Am. J. Physiol.* 272(1 Pt 1): G71–6.

Yokoyama, et al. (1995). Recovery of gastrointestinal motility from post–operative ileus in dogs: effects of Leu13–motilin (KW–5139) and prostaglandin F2 alpha. *Neurogastroenterol. Motil.* 7(4): 199–210.

De Clercq, et al. (1998). Motilin in human milk: identification and stability during digestion. *Life Sci.* 63(22): 1993–2000.

(List continued on next page.)

Primary Examiner—Lorraine Spector
Assistant Examiner—Dong Jiang
(74) *Attorney, Agent, or Firm*—Ivor R. Elrifi; David E. Johnson; Mintz Levin

(57) ABSTRACT

The use of interleukin-11 to prevent, to ameliorate, and to treat a gastrointestinal disorder in a mammal in need of such treatment is disclosed.

8 Claims, No Drawings

OTHER PUBLICATIONS

Ordaz–Jimenez et al. (1998). [Gastrointestinal hormones during minimal enteral feeding of sick premature infants] *Rev. Invest. Clin.* 50(1): 37–42. (Spanish w/ English abstract).

Jadcherla, et al. (1997). Regulation of migrating motor complexes by motilin and pancreatic polypeptide in human infants. *Pediatr. Res.* 42(3): 365–9.

Omura, et al. (1987). Macrolides with gastrointestinal motor stimulating activity. *J Med Chem.* 30(11): 1941–3.

Weich, et al (1997). Recombinant human interleukin–11 directly promotes megakaryocytopoiesis in vitro. *Blood.* 90(10): 3893–902.

Orazi, et al. (1996). Effects of recombinant human interleukin–11 ((Neumega rhIL–11 growth factor) on megakaryocytopoiesis in human bone marrow. *Exp. Hematol.* 24(11): 1289–97.

Du, et al. (1997). Protective effects of interleukin–11 in a murine model of ischemic bowel necrosis. *Am. J. Physiol.* 272(3 Pt 1): G545–52.

Orazi, et al. (1996). Interleukin–11 prevents apoptosis and accelerates recovery of small intestinal mucosa in mice treated with combined chemotherapy and radiation. *Lab. Invest.* 75(1): 33–42.

Keith, et al. (1994). "IL–11, a pleiotropic cytokine: exciting new effects of IL–11 on gastrointestinal mucosal biology." *Stem Cells.* 12 (Suppl 1):79–90.

Qiu, et al. (1996). Protection by recombinant human interleukin–11 against experimental TNB–induced colitis in rats. *Dig. Dis. Sci.* 41(8): 1625–30.

Hill, et al. (1998). Interleukin–11 promotes T cell polarization and prevents acute graft–versus–host disease after allogeneic bone marrow transplantation. *J. Clin. Invest.* 102(1): 115–23.

Redlich, et al. (1996). IL–11 enhances survival and decreases TNF production after radiation–induced thoracic injury. *J. Immunol.* 157(4): 1705–10.

Waxman, et al. (1998). Targeted hung expression of interleukin–11 enhances morine tolerance of 100% oxygen and diminishes hyperoxia–induced DNA fragmentation. *J Clin Invest.* 101(9):1970–82.

Leng and Elias (1997). Interleukin–11 inhibits macrophage interleukin–12 production. *J. Immunol.* 159(5): 2161–8.

Trepicchio, et al. (1997). IL–11 regulates macrophage effector function through the inhibition of nuclear factor–kappaB. *J. Immunol.* 159(11): 5661–70.

Trepicchio, et al. (1996). Recombinant human IL–11 attenuates the inflammatory response through down–regulation of proinflammatory cytokine release and nitric oxide production. *J. Immunol.* 157(8): 3627–34.

Taga and Kishimoto (1997). Gp130 and the interleukin–6 family of cytokines. *Annu. Rev. Immunol.* 15:797–819.

Zhang, et al. (1994). Ciliary neurotropic factor, interleukin 11, leukemia inhibitory factor, and oncostatain M are growth factors for human myeloma cell lines using the interleukin 6 signal transducer gp130. *J. Exp. Med.* 179(4):1337–42.

Yang and Yin. (1995). Interleukin (IL)–11—mediated signal transduction. *Ann. NY Acad Sci.* 762: 31–41.

Nandurkar, et al. (1996). The human IL–11 receptor requires gp130 for signalling: demonstration by molecular cloning of the receptor. *Oncogene.* 12(3):585–93.

Miyatake, et al. (1998). Complement–fixing elicited antibodies are a major component in the pathogenesis of xenograft rejection. *J. Immunol.* 160(8): 4114–23.

Yin, et al. (1994). Identification of a 130–kilodalton tyrosine–phosphorylated protein induced by interleukin–11 as JAK2 tyrosine kinase, which associates with gp130 signal transducer. *Exp. Hematol.* 22(5): 467–72.

Wang, et al. (1995). Interleukin–11 induces complex formation of Grb2. Fyn. and JAK2 in 3T3L1 cells. *J. Biol. Chem.* 270(47): 27999–8002.

Lutticken, et al. (1994). Association of transcription factor APRF and protein kinase Jak1 with the interleukin–6 signal transducer gp130. *Science* 263(5143): 89–92.

Hemmann, et al. (1996). Differential activation of acute phase response factor/Stat3 and Stat1 via the cytoplasmic domain of the interleukin 6 signal transducer gp130. *J. Biol. Chem.* 271(22): 12999–3007.

Zhong, et al. (1994). Stat3: a STAT family member activated by tyrosine phosphorylation in response to epidermal growth factor and interleukin–6, *Science* 264(5155): 95–8.

Akira (1997). IL–6–regulated trascription factors. *Int. J. Biochem. Cell Biol.* 29(12):1401–18.

Zhang, et al. (1995). Requirements of serine phosphorylation for formation for STAT–promoter complexes. *Science* 267(5206): 1990–4.

Boulton, et al. (1995). STAT3 activation by cytokines utilizing gp130 and related transducers involves a secondary modification requiring an H7–sensitive kinase. *Proc. Natl. Acad. Sci. USA.* 92(15): 6915–9.

Adunyah, et al. (1995). Interleukin–11 induces tyrosine phosphorylation, and c–jun and c–fos mRNA expression in human K562 and U937 cells. *Ann. NY Acad. Sci.* 766: 296–9.

Yin and Yang (1994). Mitogen–activated protein kinases and ribosomal S6 protein kinases are involved in signaling pathways shared by interleukin–11, interleukin–6, leukemia inhibitory factor, and oncostatin M in mouse 3T3–L1 cells. *J. Biol. Chem.* 269(5): 3731–8.

Paul, et al (1990). Molecular cloning of a cDNA encoding interleukin–11, a stromal cell–derived lymphopoietic and hematopoietic cytokine. *Proc. Natl. Acad. Sci. USA.* 87(19):7512–6.

Balkwill and Burke (1989). The cytokine network. *Immunol Today* 10(9): 299–304.

Wong and Clark (1988). Multiple actions of interleukin 6 within a cytokine network. *Immunol. Today.* (5): 137–9.

Clark and Kamen (1987). The human hematopoietic colony–stimulating factors. *Science.* 236(4806): 1229–37.

Jacobs, et al. (1970). Characteristics of a human diploid cell designated MRC–5. *Nature* 227(254): 168–70.

Opal, et al. (1999). *Blood* 93(10): 3467–72.

Ikebuchi, et al. (1988). Synergistic factors for stem cell proliferation: further studies of the target stem cells and the mechanism of stimulation by interleukin–1, interleukin–6, and granulocyte colony–stimulating factor. *Blood* 72(6): 2007–14.

Bruno, et al. (1991). Effects of recombinant interleukin 11 on human megakaryocyte progenitor cells. *Exp. Hematol.* 19(5): 378–81.

Du and Williams (1994). Interleukin–11: a multifunctional growth factor derived from the hematopoietic microenvironment. *Blood.* 83(8): 2023–30.

Yin, et al., (1992). Enhancement of in vitro and in vivo antigen–specific antibody responses by interleukin 11. *J. Exp. Med.* 175(1): 211–6.

Barton, et al. (1996). Interleukins 6 and 11 protect mice from mortality in a staphylococcal enterotoxin–induced toxic shock model. *Infect. Immun.* 64(3):714–8.

Castagliuolo, et al. (1997). IL–11 inhibits Clostridium difficile toxin A enterotoxicity in rat ileum. *Am. J. Physiol.* 273(2Pt 1): G333–41.

Liu, et al. (1996). Trophic effects of interleukin–11 in rats with experimental short bowel syndrome. *J. Pediatr. Surg.* 31(8): 1047–51.

Fiore, et al. (1998). Comparison of interleukin–11 and epidermal growth factor on residual small intestine after massive small bowel resection. *J. Pediatr. Surg.* 33(1): 24–9.

Schindel, et al. (1997). Interleukin–11 improves survival and reduces bacterial translocation and bone marrow suppresison in burned mice. *J. Pediatr. Surg.* 32(2): 312–5.

Musashi, et al. (1991). Synergistic interactions between interleukin–11 and interleukin–4 in support of proliferation of primitive hematopoietic progenitors of mice. *Blood* 78(6): 1448–51.

Burstein, et al. (1992). Leukemia inhibitory factor and interleukin–11 promote maturation of murine and human megakaryocytes in vitro. *J. Cell. Physiol.* 153(2): 305–12.

Baumann and Schendel. (1991). Interleukin–11 regulates the hepatic expression of the same plasma protein genes as interleukin–6. *J. Biol. Chem.* 266(30): 20424–7.

Kawashima, et al. (1991). Molecular cloning of cDNA encoding adipogenesis inhibitory factor and identity with interleukin–11. *FEBS Lett.* 283(2): 199–202.

Fann and Patterson. (1994). Neuropoietic cytokines and activin A differentially regulate the phenotype of cultured sympathetic neurons. *Proc. Natl. Acad. Sci. USA.* 91(1): 43–7.

Yin, et al. (1993). Involvement of IL–6 signal transducer gp130 in IL–11–mediated signal transduction. *J. Immunol.* 151(5): 2555–61.

Hibi, et al. (1990). Molecular cloning and expression of an IL–6 signal transducer, gp130. *Cell* 63(6): 1149–57.

Toyota (1998). *J. Smooth Musc. Res.* 34: 13–22.

Omura, et al. (1985). Gastrointestinal motor–stimulating activity of macrolike antibodies and the structure–activity relationship. *J. Antibiot.* (Tokyo) 38(11): 1631–2.

Depoortere, et al. (2001). *Reg. Peptides* 97: 111–9.

Depoortere, et al. (2000). *J. Pharmacol Exp. Therapeutics* 294(3): 983–90.

Depoortere, et al. (1998). *Am. Gastroenterology Soc.* (New Orleans, LA, May 16–22, 1998). (Abstract Only).

Opal, et al. (1998). Recombinant human interleukin–11 in experimental *Pseudomonas aeruginosa* sepsis in immunocompromised animals. *J. Infect. Dis.* 178(4) : 1205–8.

Girasole, et al. (1994). Interleukin–11: a new cytokine critical for osteoclast development. *J. Clin. Invest.* 93(4):1516–24.

Keith, et al. (1995). *Gastroenterology* 108(4): A846. (Abstract Only).

Keith, et al. (1994). *Gastroenterology* 106(4 part 2): (Abstract Only).

Opal, et al. (1995). *Blood* 86(10): 498A. (Abstract Only).

Sonis, et al. (1995). Alterations in the frequency, severity and duration of chemotherapy–induced mucositis in hamsters by interleukin–11. *Eur. J. Cancer B. Oral Oncol.* 31B(4): 263–6.

Leonard, et al. (1995). Prevention of experimental autoimmune encephalomyelitis by antibodies against interleukin 12. *J. Exp. Med.* 181(1): 381–6.

Scofield, et al. (1993). A hypothesis for the HLA–B27 immune dysregulation in spondyloarthropathy: contributions from enteric organisms, B27 structure. peptides bound by B27, and convergent evolution. *Proc. Natl. Acad. Sci. USA.* 90(20): 9330–4.

Hammer, et al. (1990). Spontaneous inflammatory disease in transgenic rats expressing HLA–B27 and human beta 2m: an animal model of HLA–B27–associated human disorders. *Cell.* 63(5): 1099–112.

Sonis, et al. (1995). *Proc. Am. Assoc. Cancer Res.* 36: 368 (Abstract Only).

* cited by examiner

US 6,723,314 B2

USE OF INTERLEUKIN-11 TO TREAT GASTROINTESTINAL DISORDERS

RELATED APPLICATIONS

This application is a continuation of U.S. Ser. No. 09/545,627, filed Apr. 7, 2000, which in turn claims priority to U.S. Ser. No. 60/129,421, filed Apr. 15, 1999. The contents of these applications are incorporated by reference in their entireties.

FIELD OF INVENTION

The present invention relates to the field of prevention and treatment of gastrointestinal disorders using interleukin-11. More particularly, the present invention relates to preventing or treating gastrointestinal disorders using interleukin-11 to enhance motility of the digestive tract and/or contractility of the lower esophageal sphincter.

BACKGROUND OF THE INVENTION

Motilin, a gut polypeptide hormone, causes contraction of the stomach antrum and relaxation of the pyloric sphincter, thereby promoting gastric emptying. Toyota, K., *J. Smooth Muscle Res.* (1998) 34:13–22. Central nervous system input (afferent, efferent) is not necessary for cyclic interdigestive activity or cyclic release of motilin. Siadati, M. and M. G. Sarr, *J. Gastrointest. Surg.* (1998) 2:363–72. Motilin reduces fasting gall bladder volume and increases stomach antral contractions in humans. Luiking, Y. C., et al., *Gut* (1998) 42:830–835. Motilin receptors are distributed throughout the rabbit brain, suggesting a neurotransmitter role for motilin in the brain. Depoortere, I., et al., *Brain Res.* (1997) 777:103–109.

In man, rabbit and cat, the effects of motilin and motilides are neurally mediated in vivo, whereas in vitro binding and contractility studies suggest the presence of a smooth muscular receptor. Motilin enhances contractions induced by electrical field stimulation in the rabbit antrum by a post-ganglionic interaction with the cholinergic neurotransmission in vitro at low doses and interacts directly with antral smooth muscle at high doses. Van Assche, G., et al., *Eur. J. Pharmacol.* (1997) 337:267–274. Cholinergic and NANC inhibitory nerves play an important role in human lower esophageal sphincter (LES) contraction, and motilin and cisapride may be clinically useful for improving the impaired LES of patients with gastroesophageal reflux. Tomita, R., et al., *Surg. Today* (1997) 27:985–992. Induction by motilin of phase III activity in human antrum is dependent on muscarinic mediation and the contractile effect of motilin on human duodenum involves a noncholinergic mechanism, as compared to the antral pathway. Boivin, M., et al., *Am. J. Physiol.* (1997) 272:G71–6.

Cyclical motor activity of the gastrointestinal tract, normally occurring during the interdigestive period in several mammals, is disrupted in the post-operative ileus. After laparotomy, the cyclical motor activity recovers faster in the distal intestine than in the proximal intestine and the stomach, and that KW-5139 (a motilin derivative), but not $PGF_2$-alpha (a naturally-occurring F-series prostaglandin) shortens the reappearance time of the phase III activity in the stomach. Yokoyama, T., et al., *Neurogastroenterol. Motil.* (1995) 7:199–210.

Motilin is present in human breast milk at 100 pg/ml, and in the stomach its digestion is sufficiently retarded by human milk in the newborn to exert a biological role. De Clercq, P., et al., *Life Sci.* (1998) 63:1993–2000. Minimal enteral feeding (MEF) favors secretion of gastrointestinal hormones in sick premature infants. Early MEF seems to be preferable to late one since it allows a faster secretion related to volume of the formula. Ordaz-Jimenez, M. R., et al., *Rev. Invest. Clin.* (1998) 50:37–42. Although the motilin receptor appears to be functionally present beyond 32 weeks of gestation, as assessed by in indirect pharmacologic challenge, hormonal modulation of migrating activity in the neonate by plasma motilin and pancreatic polypeptide is absent. Jadcherla, S. R., et al., *Pediatr. Res.* (1997) 42:365–9.

The exact pathophysiology of motility disorders, such as those described above, is not well understood. Consequently, a rational therapy for treating these disorders is also not available. Pharmacological agents which enhance the motility in the paralytic gut may be useful in the treatment and prevention of gastrointestinal disorders such as gastroesophageal reflux disease and surgery-induced adynamic ileus (also known as postoperative period ileus). Motility-enhancing agents (also known as gastroprokinetic agents) may also be useful in preventing or treating feeding intolerance in preterm infants.

One common approach to treating gastroesophageal reflux disease involves the use of the antiemetic agent metoclopramide, a benzamide having dopamine D2-receptor antagonist activity. Unfortunately, metoclopramide has several side effects, including an increase in prolactin levels and development of dyskinesia.

Another common practice for treating motility disorders involves the use of macrolide antibiotics, such as erythromycin. However, macrolide antibiotics are know to cause abdominal cramps and diarrhea, thus limiting their clinical application. Whether these side effects are secondary to their antibiotic activity or are due to their effect on gastrointestinal motility and secretion is not known. Various attempts to produce erythromycin derivatives having improved gastroprokinetic properties have met with limited success. See, e.g., Omura et al., *J. Med. Chem.* (1987) 30(11):1941–1943; and Omura et al., *J. Antibiotics* (1987) 38(11):1631–1632.

Thus, there remains a need for an effective, clinically applicable means of preventing or treating gastrointestinal disorders characterized by a defective motility pattern.

SUMMARY OF THE INVENTION

Applicants have for the first time determined that interleukin-11 ("IL-11") increases plasma levels of motilin, a known gastrointestinal prokinetic gut hormone. Thus, IL-11 will enhance motility in the paralytic gut and increase contractility of gastrointestinal muscles, such as the lower esophageal sphincter and stomach antrum. As a result, IL-11 can be used to treat diseases and other conditions which result from defective motility patterns, such as, for example, in treating or preventing gastroesophageal reflux disease, post-operative adynamic ileus, and feeding intolerance in preterm infants.

Provided by the present invention are methods of treating disorders where an increase in plasma level of motilin is shown to be beneficial including, without limitation, gastroesophageal reflux disease, post-operative adynamic ileus, and feeding intolerance in preterm infants.

According to the present invention, IL-11, analogs, and derivatives thereof, are administered to patients, either prophylactically or at the onset of symptoms associated with the aforementioned disorders. IL-11 can be administered in suitable pharmaceutically acceptable carriers either alone or in combination with other conventional agents useful in alleviating the symptoms associated with the aforementioned disorders.

In one embodiment, the invention comprises a method of preventing a gastrointestinal disorder which comprises administering to a mammal, prior to the on-set of symptoms, a therapeutically effective amount of interleukin-11.

In another embodiment, the invention comprises a method of treating a gastrointestinal disorder which comprises administering to a mammal experiencing a gastrointestinal disorder a therapeutically effective amount of interleukin-11.

In preferred embodiments, the therapeutic dose is effective to prevent or treat a gastrointestinal disorder resulting from defective gastrointestinal motility or reduced contractility of the lower esophageal sphincter or duodenum. Preferably, the therapeutically effective amount of interleukin-11 comprises between about 1 and 1000 µg/kg body weight, and more preferably between about 1 and 100 µg/kg body weight.

DETAILED DESCRIPTION OF THE INVENTION

The following abbreviations are used herein: interleukin-11 (IL-11); recombinant human IL-11 (rhIL-11); interleukin-12 (IL-12); tumor necrosis factor (TNF); interferon (IFN); trinitrobenzene sulfonic acid (TNBS); substance P (SP); acetylcholine (ACh); non-adrenergic non-cholinergic (NANC); lower esophageal sphincter (LES); and prostaglandin (PG).

All patent and literature references cited are incorporated herein by reference as if fully set forth.

Provided by the present invention are methods of treating disorders where an increase in plasma level of motilin is shown to be beneficial including, without limitation, gastroesophageal reflux disease, post-operative adynamic ileus, and feeding intolerance in preterm infants.

IL-11 is a stromal cell-derived pleiotropic cytokine which interacts with a variety of hematopoietic and non-hematopoietic cell types. Recombinant human IL-11 stimulates megakaryocytopoiesis in vitro and in vivo. Weich, N. S., et al. (1997) *Blood* 90:3893–3902; and Orazi, A., et al. (1996) *Exp. Hematol.* 24:1289–1297. IL-11 also stimulates erythropoiesis and regulates macrophage proliferation and differentiation. de Haan, G., et al. (1995) *Br. J. Haematol.* 90:783–790. Due to its thrombopoietic activities in vivo, IL-11 is used to treat chemotherapy-induced thrombocytopenia. Kaye, J. A. (1996) *Curr. Opin. Hematol.* 3:209–215.

In addition to its hematopoietic effects, IL-11 also protects against various forms of mucosal epithelial cell injury. For example, IL-11 has been shown to protect small intestinal cells from combined radiation, chemotherapy, and ischemia (Du, X., et al. (1997) *Am. J. Physiol.* 272:G545-G552; Orazi, A., et al. (1996) *Lab. Invest.* 75:33–42; and Keith, J. C., Jr., et al. (1994) *Stem. Cells.* (Dayt). 1(12):79–89); reduce experimental colitis induced by trinitrobenzene sulfonic acid in rat (Qiu, B. S., et al. (1996) *Dig. Dis. Sci.* 41:1625–1630); and ameliorate inflammatory bowel disease (Orazi, A., et al. (1996) *Lab. Invest.* 75:33–42). The foregoing studies show that treatment with IL-11 decreases mucosal damage, accelerates healing and improves host survival. IL-11 also reduces immune-mediated small bowel injury in acute GVHD following murine allogeneic bone marrow transplantation. Hill, G. R., et al. (1998) *J. Clin. Invest.* 102:115–123.

IL-11 has also been shown to improve survival and decrease TNF production after radiation-induced thoracic injury. Redlich, C. A., et al. (1996) *J. Immunol.* 157:1705–1710. Human IL-11, expressed as a transgene in bronchial mucosa, reduces mortality associated with hyperoxia in mice. Waxman, A. B., et al. (1998) *J. Clin. Invest.* 101:1970–1982. This enhanced murine survival may result from reduced lung injury, including alveolar-capillary protein leak, endothelial and epithelial cell membrane injury, lipid peroxidation, pulmonary neutrophil recruitment, IL-12 and TNF production, and DNA fragmentation.

The mechanisms by which IL-11 protects mucosal membranes are not fully understood. IL-11's anti-inflammatory effects are believed to result, at least in part, from down-regulation of various proinflammatory cytokines. Leng, S. X. and J. A. Elias (1997) *J. Immunol.* 159:2161–2168; Trepicchio, W. L., et al. (1997) *J. Immunol.* 159:5661–5670; and Trepicchio, W. L., et al. (1996) *J. Immunol.* 157:3627–3634. IL-11 may also cause immune deviation from a $T_H1$-like to a $TH_H2$-like phenotype, thereby alleviating immune-mediated injury. Hill, supra.

IL-11 belongs to the interleukin-6 (IL-6) family of cytokines, all of which use gp130 as a critical component for signal transduction. Taga, T. and T. Kishimoto (1997) *Annu. Rev. Immunol.* 15:797–819; Zhang, X. G., et al. (1994) *J. Exp. Med.* 179:1337–1342; and Yang, Y. C. and T. Yin (1995) *Ann. N.Y. Acad. Sci.* 762:31–40. IL-11 initiates signaling via binding to a unique IL-11-receptor-α (IL-11Rα) chain. Nandurkar, H. H., et al. (1996) *Oncogene* 12:585–593; Miyatake, T., et al. (1998) *J. Immunol.* 160:4114–4123. The IL-11/IL-11Rα complex is thought to bind to and induce clustering gp130, leading to the activation, via transphosphorylation, of associated JAKs. Yin, T., K., et al. (1994) *Exp. Hematol.* 22:467–472; Wang, X. Y., et al. (1995) *J. Biol. Chem.* 270:27999–28002. Activated JAKs phosphorylate tyrosine residues within the cytoplasmic region of gp130 which then serve as docking sites for signal transducer and activators of transcription proteins, STAT3 and STAT1. Lutticken, C., et al. (1994) *Science* 263:89–92; Hemmann, U., et al. (1996) *J. Biol. Chem.* 271:12999–13007. The activated JAKs subsequently phosphorylate tyrosine residues within the bound STAT proteins, causing the STATs to dissociate from gp130, dimerize, and enter the nucleus to act as transcriptional activators of target genes. Zhong, Z., et al. (1994) *Science* 264:95–98; Ihle, J. N. (1996) *Cell* 84:331–334; and Akira, S. (1997) *Int. J. Biochem. Cell Biol.* 29:1401–1418. STAT dimers may be additionally phosphorylated on serine or threonine residues by mitogen activated protein kinases (MAPKs) that are also activated in response to cytokine binding to the receptor. Zhang, X., et al. (1995) *Science* 267:1990–1994; Boulton, T. G., et al. (1995) *Proc. Natl. Acad. Sci. U.S.A.* 92:6915–6919; Adunyah, S. E., et al. (1995) *Ann. N.Y. Acad. Sci.* 766:296–299; and Yin, T. and Y. C. Yang (1994) *J. Biol. Chem.* 269:3731–3738. This additional phosphorylation may potentiate STAT function as an activator of transcription.

IL-11 is described in detail in International Application PCT/US90/06803, published May 30, 1991; as well as in U.S. Pat. No. 5,215,895; issued Jun. 1, 1993. A cloned human IL-11 was previously deposited with the ATCC, 10801 University Boulevard, Manassa, Va. 20110–2209, on Mar. 30, 1990 under ATCC No. 68284. Moreover, as described in U.S. Pat. No. 5,270,181; issued Dec. 14,1993; and U.S. Pat. No. 5,292,646; issued Mar. 8, 1994; IL-11 may also be produced recombinantly as a fusion protein with another protein. IL-11 can be produced in a variety of host cells by resort to now conventional genetic engineering techniques. In addition, IL-11 can be obtained from various cell lines, for example, the human lung fibroblast cell line, MRC-5 (ATCC Accession No. CCL 171) and Paul et al., the human trophoblastic cell line, TPA30-1 (ATCC Accession No. CRL 1583). Described in Proc Natl Acad Sci USA 87:7512 (1990) is a cDNA encoding human IL-11 as well as the deduced amino acid sequence (amino acids 1 to 199). U.S. Pat. No. 5,292,646, supra, describes a des-Pro form of IL-11 in which the N-terminal proline of the mature form of IL-11 (amino acids 22–199) has been removed (amino acids 23–199). As is appreciated by one skilled in the art, any form of IL-11, which retains IL-11 activity, is useful according to the present invention.

In addition to recombinant techniques, IL-11 may also be produced by known conventional chemical synthesis. Methods for constructing the polypeptides useful in the present invention by synthetic means are known to those of skill in the art. The synthetically constructed cytokine polypeptide sequences, by virtue of sharing primary, secondary, or tertiary structural and conformational characteristics with the natural cytokine polypeptides are anticipated to possess biological activities in common therewith. Such synthetically constructed cytokine polypeptide sequences or fragments thereof, which duplicate or partially duplicate the functionality thereof may also be used in the method of this invention. Thus, they may be employed as biologically active or immunological substitutes for the natural, purified cytokines useful in the present invention.

Modifications in the protein, peptide or DNA sequences of these cytokines or active fragments thereof may also produce proteins which may be employed in the methods of this invention. Such modified cytokines can be made by one skilled in the art using known techniques. Modifications of interest in the cytokine sequences, e.g. the IL-11 sequence, may include the replacement, insertion or deletion of one or more selected amino acid residues in the coding sequences. Mutagenic techniques for such replacement, insertion or deletion are well known to one skilled in the art. (See, e.g., U.S. Pat. No. 4,518,584.)

Other specific mutations of the sequences of the cytokine polypeptides which may be useful therapeutically as described herein may involve, e.g., the insertion of one or more glycosylation sites. An asparagine-linked glycosylation recognition site can be inserted into the sequence by the deletion, substitution or addition of amino acids into the peptide sequence or nucleotides into the DNA sequence. Such changes may be made at any site of the molecule that is modified by addition of O-linked carbohydrate. Expression of such altered nucleotide or peptide sequences produces variants which may be glycosylated at those sites.

Additional analogs and derivatives of the sequence of the selected cytokine which would be expected to retain or prolong its activity in whole or in part, and which are expected to be useful in the present method, may also be easily made by one of skill in the art. One such modification may be the attachment of polyethylene glycol (PEG) onto existing lysine residues in the cytokine sequence or the insertion of one or more lysine residues or other amino acid residues that can react with PEG or PEG derivatives into the sequence by conventional techniques to enable the attachment of PEG moieties.

Additional analogs of these selected cytokines may also be characterized by allelic variations in the DNA sequences encoding them, or induced variations in the DNA sequences encoding them. It is anticipated that all analogs disclosed in the above-referenced publications, including those characterized by DNA sequences capable of hybridizing to the disclosed cytokine sequences under stringent hybridization conditions or non-stringent conditions (Sambrook et al., Molecular Cloning. A Laboratory Manual, 2d edit., Cold Spring Harbor Laboratory, New York (1989)) will be similarly useful in this invention.

Also considered useful in these methods are fusion molecules, prepared by fusing the sequence or a biologically active fragment of the sequence of one cytokine to another cytokine or proteinaceous therapeutic agent, e.g., IL-11 fused to IL-6 (see, e.g., methods for fusion described in PCT/US91/06186 (WO92/04455), published Mar. 19, 1992). Alternatively, combinations of the cytokines may be administered together according to the method.

Thus, where in the description of the methods of this invention IL-11 is mentioned by name, it is understood by those of skill in the art that IL-11 encompasses the protein produced by the sequences presently disclosed in the art, as well as proteins characterized by the modifications described above yet which retain substantially similar activity.

Pharmaceutical compositions containing IL-11 which are useful in practicing the methods of the present invention may also contain pharmaceutically acceptable carriers, diluents, fillers, salts, buffers, stabilizers and/or other materials well-known in the art. The term "pharmaceutically acceptable" means a material that does not interfere with the effectiveness of the biological activity of the active ingredient(s) and that is not toxic to the host to which it is administered. The characteristics of the carrier or other material will depend on the route of administration.

It is currently contemplated that the various pharmaceutical compositions should contain about 0.1 micrograms to about 1 milligram per milliliter of the active ingredient.

Administration can be carried out in a variety of conventional ways. Intraperitoneal injection is the preferred method of administration. Intravenous, cutaneous or sub-cutaneous injection may also be employed. For injection, IL-11 will preferably be administered in the form of pyrogen-free, parenterally acceptable aqueous solutions. The preparation of such parenterally acceptable protein solutions, having due regard to pH, isotonicity, stability and the like, is within the skill of the art.

The amount of IL-11 used for treatment will depend upon the severity of the condition, the route of administration, the reactivity or activity of the active ingredient, and ultimately will be decided by the treatment provider. In practicing the methods of treatment of this invention, a therapeutically effective amount of IL-11 is administered. The term "therapeutically effective amount" means the total amount of each active component of the method or composition that is sufficient to show a meaningful patient benefit (e.g., curing, ameliorating, inhibiting, delaying or preventing onset of, preventing recurrence or relapse of). One common technique to determine a therapeutically effective amount for a given patient is to administer escalating doses periodically until a meaningful patient benefit is observed by the treatment provider. When applied to an individual active ingredient, administered alone, the term refers to that ingredient alone. When applied to a combination, the term refers to combined amounts of the active ingredients that result in the therapeutic effect, whether administered in combination, serially or simultaneously. A therapeutically effective dose of IL-11 in this invention is contemplated to be in the range of about 1 to about 1000 $\mu$g/kg body weight, and more preferably between about 1 and about 100 $\mu$g/kg body weight. The number of administrations may vary, depending on the individual patient and the severity of the gastrointestinal disorder.

EXAMPLES

Example 1

Effect of IL-11 on TNBS-induced Colitis in Rabbits

IL-11 is believed to attenuate the inflammatory response via a reduction of the release of pro-inflammatory cytokines (TNF-α, IL-1β, IL-12 and IFN-γ) and of nitric oxide production by macrophages. Trepicchio, W. L., et al., *J. Immunol.* (1997) 157:3627–3634; *J. Immunol.* (1997) 159:5661–5670. This example demonstrates that IL-11 affects inflammatory changes in the deeper, neuromuscular layers of the gut wall. Specifically, this example shows the effects of treatment with IL-11 in New Zealand rabbits with colitis induced by intrarectal application of TNBS. Muscle strips from the inflamed region have an increased passive tension, and a decreased contractile response to ACh, motilin, SP and potassium ion. Subcutaneous infusion of 40 μg/kg per day IL-11 (or more), for 5 days following induction of inflammation, normalizes the contractile parameters. The response towards motilin and SP was normalized with a dose of 40 μg/kg per day; the response to ACh and potassium ion was normalized with a dose of 720 μg/kg per day. The decrease in motilin and SP receptor density was also reversed by IL-11 treatment. Treatment with IL-11 dose-dependently decreased weight in these rabbits. Depoortere, I., et al., *Am. Gastroenterology Soc.* (New Orleans, La., May 16–22, 1998).

Example 2

Effect of IL-11 on Plasma and Tissue Concentrations of Motilin and SP

The effects of IL-11 treatment on plasma and tissue concentrations of motilin and SP present in endocrine cells and/or neurons of the gut wall were investigated. Depoortere, I., et al., *Am. Gastroenterology Soc.* (to be presented May 15–20, 1999, Orlando, Fla.). Rabbits received 4, 40, 72 or 720 μg/kg recombinant IL-11 sc. or saline (control). One hour later, colitis was induced with 135 mg/kg TNBS and a sc. infusion of 4, 40, 72 or 720 μg/kg per day IL-11 or saline was started for 5 days. SP and motilin were measured by RIA, before the induction of inflammation and just before the rabbits were sacrificed, in plasma and in extracts prepared from the mucosa of the duodenum and the colon and from the muscle layer of the colon. mRNA levels were determined by semi-quantitative RT-PCR. IL-11 concentrations were measured by ELISA. Plasma motilin levels were not influenced by the inflammatory process (649±69 vs 724±126 pg/ml). The motilin content was increased from 381±78 to 664±74 ng/g tissue in the duodenal mucosa, but not in the mucosa (64±4 vs 78±12 ng/g tissue) or muscle layer (24±4 vs 17±1 ng/g tissue) of the inflamed colon. Inflammation also increased motilin MRNA expression 2.5 fold in the duodenal mucosa. In contrast, plasma SP levels were decreased from 1812±60 to 635±101 pg/ml, SP content in the muscle layer of the colon from 45±8 to 7±2 ng/g tissue. In the duodenal or colonic mucosa SP content was unchanged. Treatment of rabbits during colitis with IL-11 (4, 40, 72, 720 μg/kg per day) resulted at day 5 in an increase in plasma IL-11 levels of respectively 218±91, 5345±1876, 10221±2175, 116527±25461 pg/ml and increased plasma motilin levels with 199±77, 799±201, 1740±560 and 2084±797 pg/ml. IL-11 treatment also dose-dependently augmented the motilin content in the duodenal mucosa from 664±74 (TNBS) to 783±65, 1070±60, 1176±148 and 1273±50 ng/g tissue. Similar observations were made in the colonic mucosa but not in the colonic muscle layer. This increase was not reflected in a further increase in motilin mRNA expression. However, a stimulatory effect of IL-11 was not observed on plasma SP levels which were still decreased to 848 pg/ml with the highest dose of IL-11 tested, nor on the SP content in the duodenal or colonic mucosa. Only in the colonic muscle layer a small but significant increase was observed with low doses of IL-11. IL-11 treatment during colitis markedly increased plasma motilin levels and the motilin content in the mucosa of the duodenum and the colon. However, this effect was not observed with SP suggesting that it is due to a specific interaction of IL-11 with the motilin endocrine cell which does not occur at the level of the motilin mRNA expression.

While the present invention has been described in terms of specific methods and compositions, it is understood that variations and modifications will occur to those skilled in the art upon consideration of the present invention. Numerous modifications and variations in the invention as described in the above illustrative examples are expected to occur to those skilled in the art and, consequently, only such limitations as appear in the appended claims should be placed thereon. Accordingly, it is intended in the appended claims to cover all such equivalent variations which come within the scope of the invention as claimed.

What is claimed:

1. A method for treating a gastrointestinal motility disorder in a mammal which comprises administering to the mammal a therapeutically active amount of interleukin-11, wherein said gastrointestinal motility disorder is selected from the group consisting of gastroesophageal reflux disease, post-operative adynamic ileus and intolerance to oral feeding.

2. The method of claim 1, wherein the therapeutically effective amount of interleukin-11 comprises 1 to 1000 μg/kg body weight.

3. The method of claim 1, wherein the therapeutically effective amount of interleukin-11 comprises 1 to 100 μg/kg body weight.

4. The method of claim 1, wherein the interleukin-11 is administered daily until improvement of the disorder is observed.

5. The method of claim 1, wherein the interleukin-11 is administered daily until remission of the disorder is observed.

6. The method of claim 1, wherein the gastrointestinal disorder is gastroesophageal reflux disease.

7. The method of claim 1, wherein the gastrointestinal motility disorder is post-operative adynamic ileus.

8. The method of claim 1, wherein said subject is a preterm infant and said gastrointestinal disorder is intolerance to oral feeding.

* * * * *